United States Patent
Hestad

(10) Patent No.: US 8,052,728 B2
(45) Date of Patent: Nov. 8, 2011

(54) METHOD FOR STABILIZING A FACET JOINT

(75) Inventor: Hugh D. Hestad, Edina, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 998 days.

(21) Appl. No.: 11/831,780

(22) Filed: Jul. 31, 2007

(65) Prior Publication Data

US 2009/0036926 A1    Feb. 5, 2009

(51) Int. Cl.
*A61B 17/88* (2006.01)
(52) U.S. Cl. ......... 606/279; 606/247; 606/249; 128/898
(58) Field of Classification Search ................... 606/246, 606/247, 249, 279; 623/17.11–17.16; 128/898
See application file for complete search history.

(56) References Cited

U.S. PATENT DOCUMENTS

| | | |
|---|---|---|
| 4,911,718 A | 3/1990 | Lee et al. |
| 5,147,404 A | 9/1992 | Downey |
| 5,171,284 A | 12/1992 | Brånemark |
| 5,306,310 A | 4/1994 | Siebels |
| 5,571,191 A | 11/1996 | Fitz |
| 6,099,565 A | 8/2000 | Sakura, Jr. |
| 6,296,664 B1 | 10/2001 | Middleton |
| 6,342,076 B1 | 1/2002 | Lundborg |
| 6,436,142 B1 | 8/2002 | Paes et al. |
| 6,451,057 B1 | 9/2002 | Chen et al. |
| 6,610,094 B2 | 8/2003 | Husson |
| 6,660,037 B1 | 12/2003 | Husson et al. |
| 6,966,930 B2 | 11/2005 | Arnin et al. |
| 2003/0004572 A1 | 1/2003 | Goble et al. |
| 2004/0167625 A1 | 8/2004 | Beyar et al. |
| 2004/0220296 A1 | 11/2004 | Lowman et al. |
| 2005/0085912 A1 | 4/2005 | Arnin et al. |
| 2005/0177240 A1 | 8/2005 | Blain |
| 2006/0004358 A1 | 1/2006 | Serhan et al. |
| 2006/0009851 A1 | 1/2006 | Collins et al. |
| 2006/0036323 A1 | 2/2006 | Carl et al. |
| 2006/0084985 A1 | 4/2006 | Kim |
| 2006/0085068 A1 | 4/2006 | Barry |
| 2006/0085070 A1 | 4/2006 | Kim |
| 2006/0111779 A1 | 5/2006 | Petersen |
| 2006/0173464 A1 | 8/2006 | Ellman et al. |
| 2006/0190081 A1 | 8/2006 | Kraus et al. |
| 2007/0043361 A1* | 2/2007 | Malandain et al. ............. 606/61 |
| 2008/0177309 A1* | 7/2008 | McLeer ........................ 606/247 |

FOREIGN PATENT DOCUMENTS

WO      WO0130248 A1      5/2001

* cited by examiner

*Primary Examiner* — Thomas C. Barrett
*Assistant Examiner* — Christina Negrelli
(74) *Attorney, Agent, or Firm* — Seager Tufte Wickhem LLC

(57) ABSTRACT

The present invention relates to methods and spinal implant devices for stabilizing a facet joint. In one embodiment, the method includes forming a hole through a facet joint and respective overlapping superior and inferior articular processes of adjacent vertebra which, respectively, include superior articular process and inferior articular process openings. A spinal implant device, such as elongated member, is inserted lengthwise into the hole. The first end portion of the elongated member defines a closed end and the second end portion defines an open end permitting entry into an interior of the member. The interior of the elongated member is filled with a desired material to expand the first and second end portions of the member beyond respective superior articular process and inferior articular process openings of the hole to greater than a desired size of the superior articular process and inferior articular process openings to stabilize the facet joint.

12 Claims, 4 Drawing Sheets

METHOD FOR STABILIZING A FACET JOINT

FIELD OF THE INVENTION

The present invention relates to facet joint treatment, and, more particularly, to methods and spinal implant devices for stabilizing a facet joint.

BACKGROUND OF THE INVENTION

Disorders of the spine can cause extreme and debilitating pain. The disorder may be due to trauma, inflammation, or degeneration of any one of a number of spinal components. One such spinal component that can be a significant source of spinal disorders is the facet joint, which is a diarthroidal joint that provides both sliding articulation and load transmission features while preventing excessive torsion of the spine. By way of example, a patient may suffer from arthritic facet joints, severe facet joint tropism, otherwise deformed facet joints, facet joint injuries, etc. These disorders can lead to spinal stenosis, degenerative spondylolithesis, and/or isthmic spondylotlisthesis, causing pinching of the nerves that extend between the affected vertebrae. In addition, problems with the facet joints can complicate treatments associated with other portions of the spine. For example, contraindications for intervertebral disc replacement include arthritic facet joints, absent facet joints, severe facet joint tropism, or otherwise deformed facet joints. Also, disorders in an intervertebral disc often will lead to disorders in the facet joint, and vice-versa.

The demand for pain relief from those who suffer from back pain has spurred technological development. To this end, various technologies and approaches have been developed to treat spinal pain, including disorders associated with facet joints. One treatment is a facetectomy, which is removal of the facet joint. A facetectomy may provide some pain relief. However, the facet joints partially support axial, torsional, and shear loads that act on the spinal column. Thus, their removal inhibits natural spinal function and may lead to increased instability of the spine. Fusion is another treatment for the facet joint. Fusion is usually completed as part of a fusion of adjacent vertebrae to stabilize the spine at the fused location. Other treatments include surgically implanting artificial devices either to replace or support the facet joints. Unfortunately, the currently available implants require invasive surgery. Moreover, they do not adequately address all of the mechanics of motion for the spinal column and many have a tendency to migrate from their installed location under normal patient activity.

There is thus a need for noninvasive methods for stabilizing facet joints while improving patient recovery time and implant stability.

SUMMARY OF THE INVENTION

The present invention provides methods and spinal implant devices for stabilizing a facet joint.

In one embodiment, a method for stabilizing a facet joint includes forming a hole through a facet joint and respective overlapping superior and inferior articular processes of adjacent vertebra which, respectively, include superior articular process and inferior articular process openings. The hole extends lengthwise between the superior articular process and inferior articular process openings.

Next, a spinal implant device such as elongated member, e.g., an elongated bag, is inserted lengthwise into the hole to position opposing first and second end portions of the member proximate either the superior articular process and inferior articular process openings, respectively, or the inferior and superior articular process openings, respectively. The first end portion of the elongated member defines a closed end and the second end portion defines an open end permitting entry into an interior of the member. The elongated member may optionally include a central portion between opposing first and second end portions that is configured to expand.

The interior of the elongated member then is filled with a desired material to expand the first and second end portions of the member beyond respective superior articular process and inferior articular process openings of the hole to greater than a desired size of the superior articular process and inferior articular process openings to stabilize the facet joint. If the elongated member includes the optional central portion, the central portion expands beyond the hole within the facet joint thereby distracting the inferior and superior articular processes.

Accordingly, the in-situ spinal implant device, which stabilizes the facet joint, includes an elongated member, e.g., an elongated bag, situated lengthwise through a hole of a facet joint and respective overlapping inferior and superior articular processes of adjacent vertebra which, respectively, include inferior articular process and superior articular process openings. The elongated member includes opposing first and second end portions defining closed ends with an intermediate portion extending therebetween and through the hole. The first and second end portions are filled with a desired material and expanded beyond either the inferior articular process and superior articular process openings, respectively, or the superior articular process and inferior articular process openings to greater than a desired size of respective inferior articular process and superior articular process openings to stabilize the facet joint. The intermediate portion of the member optionally includes a central portion that is filled with the desired material and expanded beyond the hole within the facet joint thereby distracting the inferior and superior articular processes.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

FIGS. 1-4 depict methods and spinal implant devices 10 for stabilizing a facet joint 12. The facet joint 12, which supports an intervertebral disc 14 during extension and flexion motion as well as lateral bending while under axial loading, for example, can degenerate over time leading to pain, which can be caused by pinched nerves. As such, treatment methods to stabilize the facet joint 12 may be necessary to relieve pain and restore facet joint function.

Figure 1:
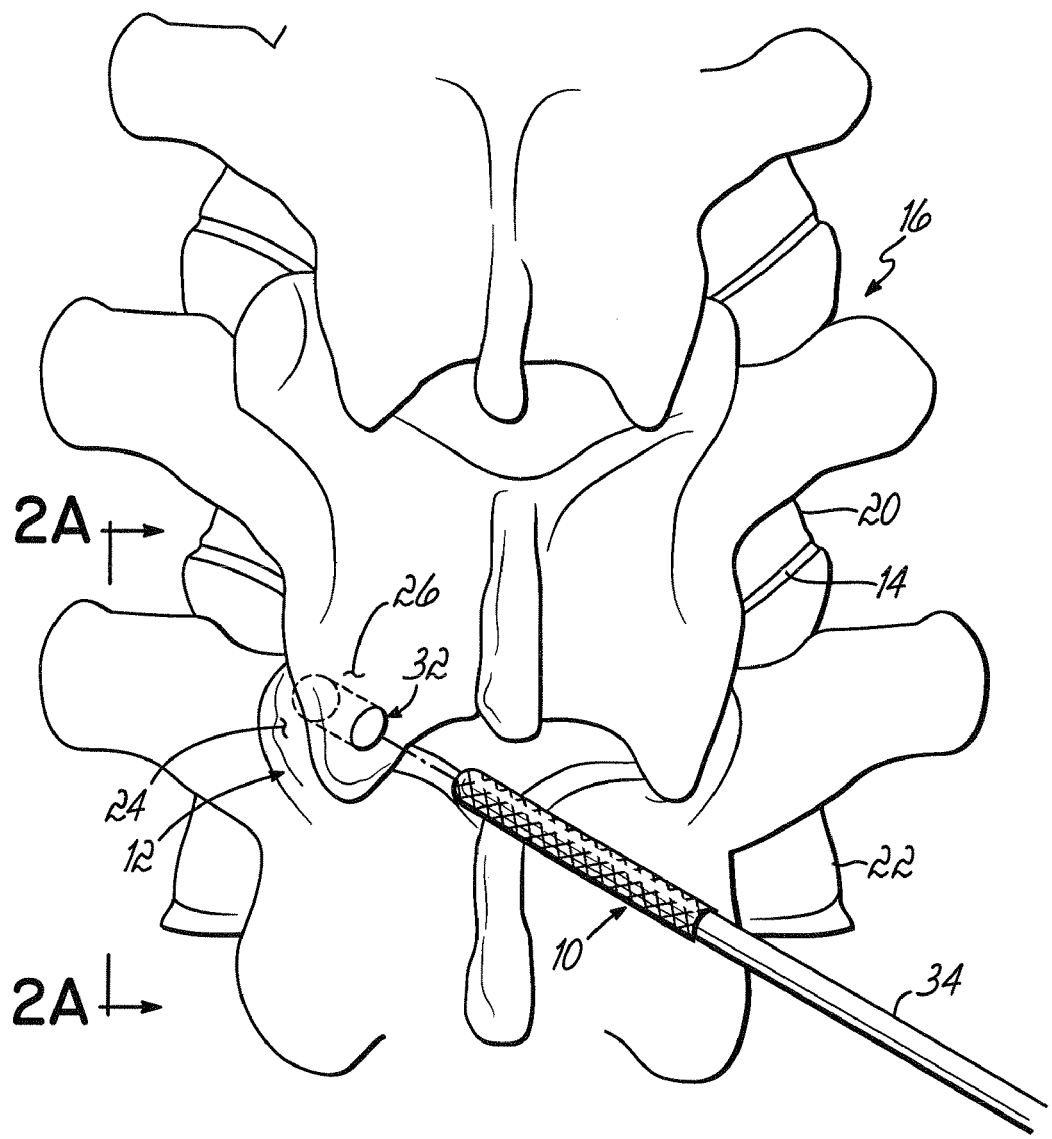
FIG. 1 depicts an anterior view of adjacent vertebra with a facet joint having a hole therethrough, and a delivery catheter having attached thereto an embodiment of an elongated member for lengthwise insertion into the hole.

To that end, as best shown in FIG. 1, a portion of a spine 16 includes adjacent vertebra 20 and 22 with intervertebral disc 14 situated therebetween, and superior and inferior articular processes 24 and 26 having facet joint 12 situated therebetween. The facet joint 12 and respective overlapping superior and inferior articular processes 24, 26 (and corresponding superior and inferior facets 28 and 30 (See FIGS. 2A-2E)) have a hole 32 formed therethrough for receiving elongated member 10, such as an elongated bag, by way of a delivery catheter 34 for stabilizing the facet joint 12, as further described next.

Figure 2A:
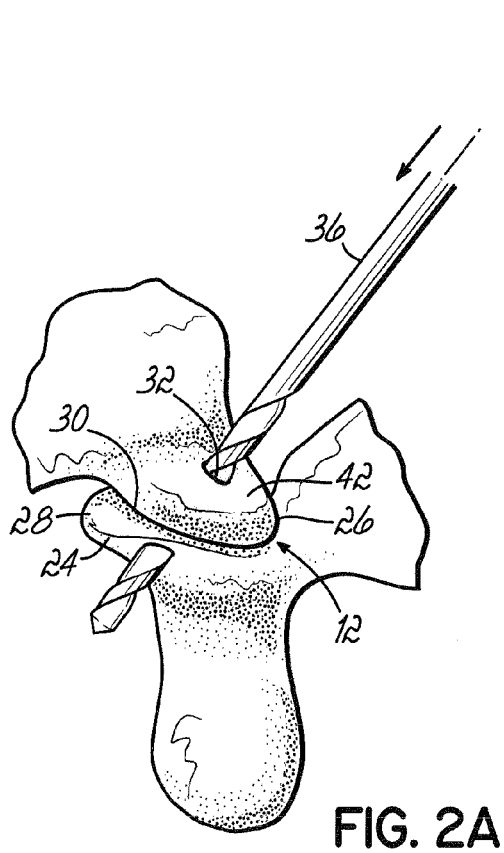
FIG. 2A depicts formation of the hole of FIG. 1, by drilling posteriorly through the facet joint.

In one embodiment, the method for stabilizing the facet joint 12 generally includes percutaneously locating the facet joint 12 posteriorly then creating access with a small incision or puncture through tissue to expose the inferior articular process 26 of the vertebra 20. Once located, a surgeon can drill a hole 32 posteriorly through the facet joint 12, as best shown in FIG. 2A. In one example, a cannulated drill 36 may be used for drilling through the inferior articular process 26 (including the inferior articular facet 30) of vertebra 20, the facet joint 12, and the superior articular process 24 (including the superior articular facet 28) of the adjacent vertebra 22. FIG. 2A shows only one possible trajectory through the facet joint 12. However, other possible trajectories and entry locations, such as via the superior articular process 24, are possible and may be preferred depending on the patient and location along the spine of the desired facet joint(s).

Figure 2B:
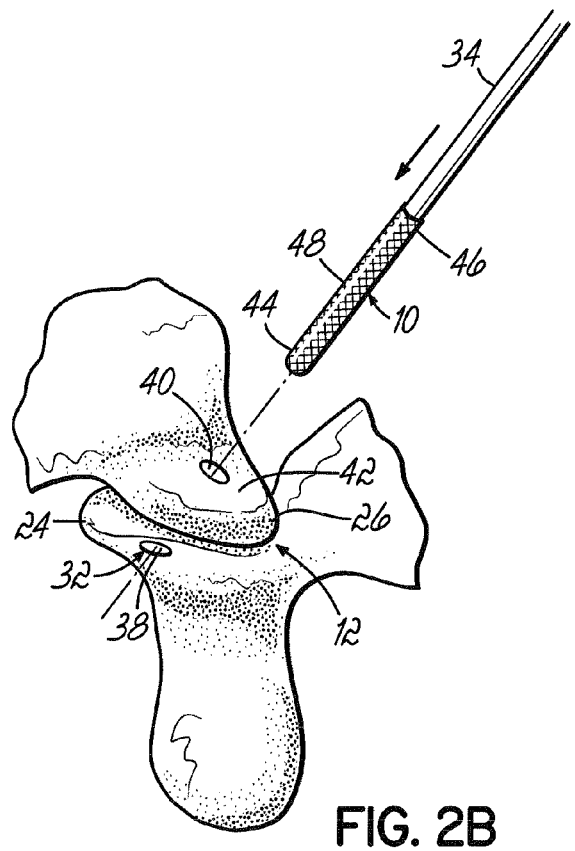
FIG. 2B depicts delivery of the elongated member of FIG. 1 into the hole drilled in FIG. 2A.

With reference to FIG. 2B, the hole 32 has been formed posteriorly through the facet joint 12 and respective overlapping superior and inferior articular processes 24, 26 of adjacent vertebra 20, 22 (not shown). In addition, the hole 32 includes opposing superior articular process and inferior articular process openings 38 and 40 of a desired size, respectively, in outer surfaces 42 of the superior and inferior articular processes 24, 26. After the hole 32 is formed, the surgeon can insert the elongated bag 10 into the hole 32 lengthwise. To that end, the delivery catheter 34 has the elongated bag 10 attached thereto by means known in the art for lengthwise insertion into the hole 32, as shown in FIG. 2C.

Figure 3:
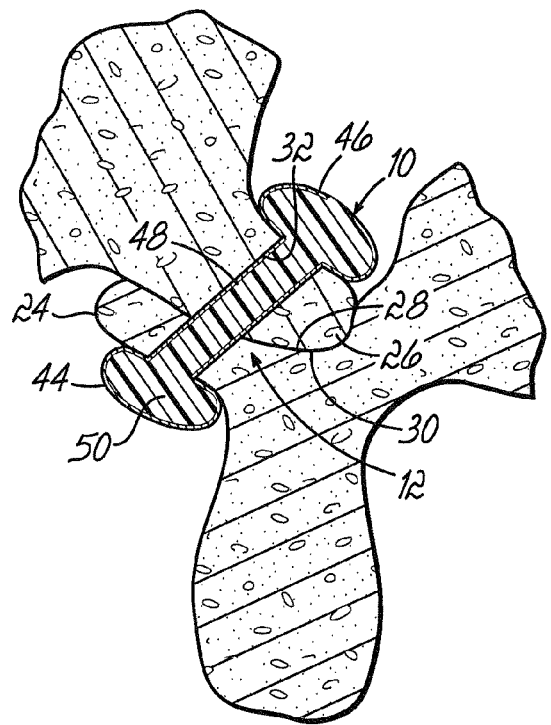
FIG. 3 depicts a cross-sectional view of the elongated member of FIG. 2E taken along a longitudinal axis of the member through the superior and inferior articular facets.

The elongated bag 10, as shown in FIGS. 2B and 3, includes opposing first and second end portions 44, 46 with an intermediate portion 48 extending therebetween. The first end portion 44 defines a closed end and the second end portion 46 defines an open end permitting entry into an interior of the bag 10. Generally, the first end portion 44 is first inserted into the hole 32. The bag 10 is configured to hold a desired material 50 within the interior thereof, with the first and second end portions 44, 46 of the bag 10 configured to expand. The intermediate portion 48 may also expand. With further reference to FIG. 2B, the second end portion 46, or open end, of the elongated bag 10 is secured to a distal end of the catheter 34, which has a lumen (not shown) therethrough. Such lumen includes a distal opening in the distal end that is in fluid communication with the interior of the bag 10 for delivering the desired material 50 into the bag 10.

Although a delivery catheter 34 is shown in FIG. 2B, one having ordinary skill in the art will recognize that the elongated bag 10 may be placed over a guidewire, e.g., a K wire, for placement within the hole 32. In another embodiment, to facilitate accurate placement, the catheter 34 may have a release mechanism to disengage the elongated bag 10 from the delivery catheter 34. In addition, to enable the surgeon to position the elongated bag 10 properly, the catheter 34 may have a positive stop or the catheter 34 may have markers on it for radiographic assessment of the elongated bag's position. In any case, a means for accurate positioning of the elongated bag 10 in the hole 32 may be used to ensure the proper placement of the elongated bag 10 within the hole 32. The means may be included on the catheter 34 or on the elongated bag 10.

Figure 2C:
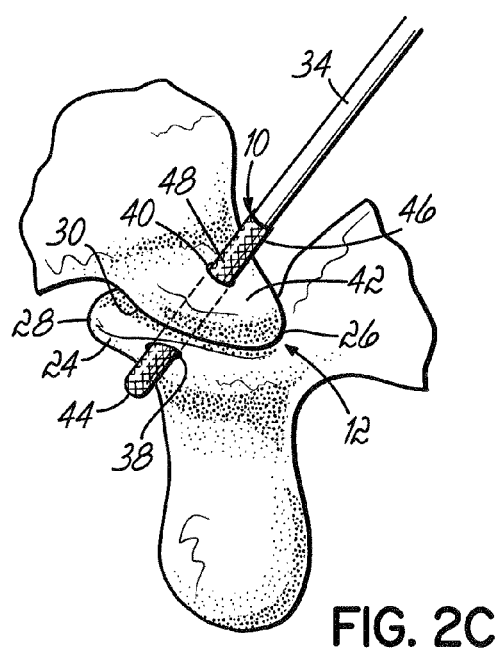
FIG. 2C depicts the elongated member of FIG. 2B positioned lengthwise in the hole.

With reference now to FIG. 2C, the elongated bag 10 is positioned lengthwise into the hole 32 wherein the first end portion 44, or closed end, is first inserted into the hole 32. The first end portion 44 is positioned proximate the superior articular process opening 38 and the second end portion 46 is positioned proximate the inferior articular process opening 40 of the hole 32. The elongated bag 10 is dimensioned to extend from the inferior articular process opening 40 to the superior articular process opening 38. The bag length may be at least about equal to the distance between the openings 38, 40 with the expansion of the bag 10 causing it to expand beyond the superior articular process and inferior articular process openings 38, 40. In another embodiment, the length is greater than the distance between the superior articular process and inferior articular process openings 38, 40, such that radial expansion of the bag 10 causes it to expand beyond the superior articular process and inferior articular process openings 38, 40.

The elongated bag 10 may be woven from fibers such as polymethyl methacrylate, polyethylene, polypropylene, polyolefin copolymers, polycarbonates, polyesters, ether-ketone copolymers, polytetrafluoroethylene fibers, silk, or other flexible, biocompatible materials, for example. The elongated bag 10 also may be porous or permeable to the desired material 50. Thus, a portion of the desired material 50 may escape the elongated bag 10 to bond or otherwise interact with the joint or bone. In another embodiment, the bag 10 may be made of wire mesh. The wire mesh can be titanium, stainless steel, NiTiNOL, or the like, for example. The bag 10 may be constructed or woven to have a natural dumbbell shape. In this configuration, the bag 10 may be held in an elongated insertion shape during insertion thereof then revert to its natural dumbbell shape following positioning of the implant through the holes in the adjacent facets. NiTiNOL is one material that can be used to achieve the dumbbell shape.

In additional embodiments, the elongated bag 10 may be made of a combination of materials. By way of example, one combination can be a combination of a polymeric fiber and a metallic material; e.g., an aramid material and a metallic material such as titanium.

Figure 2D:
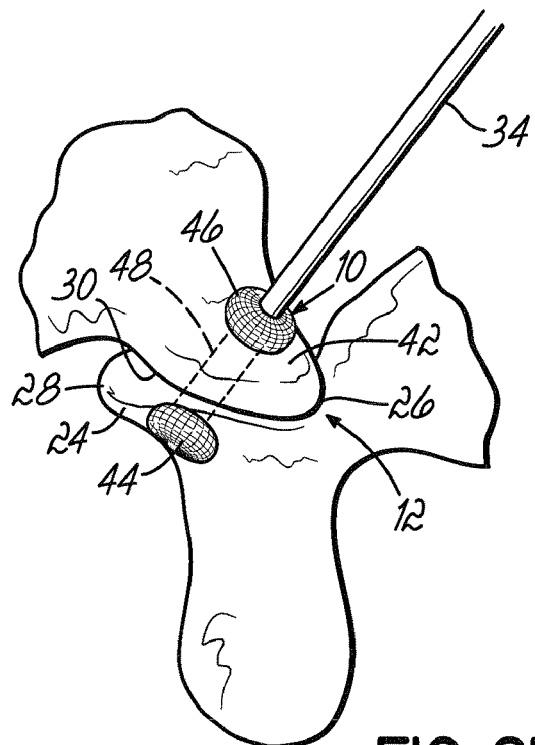
FIG. 2D depicts filling the elongated member of FIG. 2C via the delivery catheter to expand opposing first and second end portions of the member, respectively, beyond superior articular process and inferior articular process openings of the hole to greater than the size of those openings.
Figure 2E:
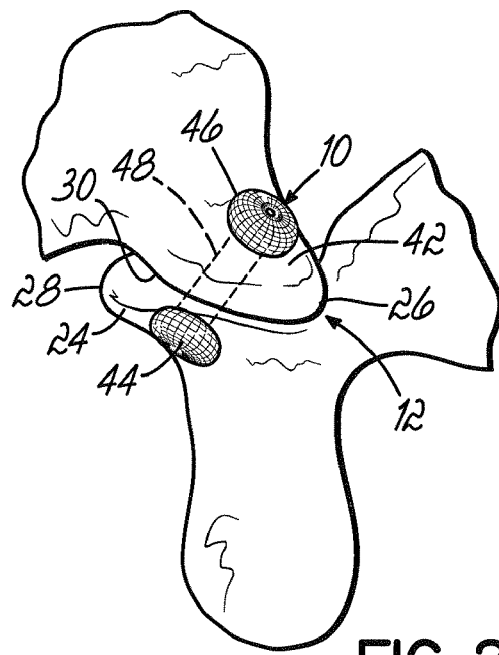
FIG. 2E depicts the member of FIG. 2D after removal of the delivery catheter.

As previously mentioned, following insertion, the elongated bag 10 is filled with the desired material 50. FIG. 2D depicts using the delivery catheter 34 to deliver the desired material 50 to the interior of the elongated bag 10 through the second end 46. Specifically, the desired material 50 travels through the lumen and exits the distal opening in the distal end of the catheter 34 that is in fluid communication with the interior of the bag 10 for delivering the desired material 50 into the bag 10. The desired material 50 fills the bag 10 and expands the opposing first and second end portions 44, 46, respectively, beyond the superior articular process and inferior articular process openings 38, 40 of the hole 32. The desired material 50 may also cause the intermediate portion 48 to enlarge and fill the hole 32. The opposing first and second end portions 44, 46 expand to greater than the size of the superior articular process and inferior articular process openings 38, 40 to stabilize the facet joint 12. Consequently, the ends 44, 46 are sized greater than the hole 32 to prevent removal of the bag 10 from the hole 32. While the figures generally depict the elongated bag 10 as symmetrical prior to and after filling, one skilled in the art will observe that the elongated bag 10 may have other configurations. By way of example, the elongated bag 10 may have a shape that conforms to the patient's anatomy or one that provides a particular compressive load to the facet joint 12. In one embodiment, the filled bag 10 maintains the superior and inferior facets 28, 30 in an adjoining relationship possibly to promote fusion or as one component of a 360° fusion procedure.

The desired material 50 for filling the bag 10 may include bone cement or in-situ curable polymeric materials including, for example, elongated polymeric materials, polymeric beads, hydrogel materials, fusion promoting materials, autograft bone, allograft bone, xenograft bone, or any combination thereof. Furthermore, other desired materials capable of bearing loads may include poly(lactic acid), poly (glycolic acid), p-dioxanon fibers, polyarylethyl, polymethyl methacrylate, polyurethane, amino-acid-derived polycarbonate, polycaprolactone, aliphatic polyesters, calcium phosphate, unsaturated linear polyesters, vinyl pyrrolidone, polypropylene fumarate diacrylate, or mixtures thereof, for example With reference to FIG. 2E, once the bag 10 is filled, the delivery catheter 34 (not shown) may be removed. The second end 46, or open end, of the bag 10 may be sealed or cinched tight, such as by means known in the art using, for example, the catheter 34. Alternatively, the second end 46 of the bag 10 may not require sealing. For example, depending on the choice of the desired material 50 that fills the bag 10, the desired material 50 may cure or harden such that no sealing of the second end 46 of the bag 10 itself is required. In another embodiment where the elongated bag 10 is made of a shape memory material, the bag 10 may not require a separate step of sealing. For example, the second end 46 may close on its own volition upon removal of the delivery catheter 34. Once the bag 10 is filled and the catheter 34 removed, the initial incision made by the surgeon may be finally closed.

Accordingly, as best shown in FIG. 3, the inferior articular process 26 and superior articular process 24 are held in an enjoining position by the bag 10 filled with the desired material 50. In one embodiment, the filled bag maintains the superior and inferior facets 28, 30 in an adjoining relationship possibly to promote fusion or as one component of a 360° fusion procedure. The elongated bag 10 of the present invention may also be used in conjunction with an interbody device, such as BAK/C® and BAK® Interbody Fusion Systems, PEEK or Trabecular Metal™ implants available from Zimmer Spine, Inc., of Minneapolis, Minn., to treat both the posterior and anterior of the spine. In another embodiment, the elongated bag 10 may be used in conjunction with a dynamic stabilization system to maximize the natural biomechanics of the spine. Depending upon choice of the desired material 50, the filled bag may be rigid such that during normal extension, flexion, lateral bending and other physiological motion, the articular processes 24, 26 do not move relative to one another. Alternatively, by selecting a flexible material, such as a compressible, elastic material or constrained elastic material, relative movement between the superior and inferior facets 28, 30 may occur. Furthermore, the degree of flexibility may be designed or customized for each patient or according to the patient's diagnosis.

Figure 4:
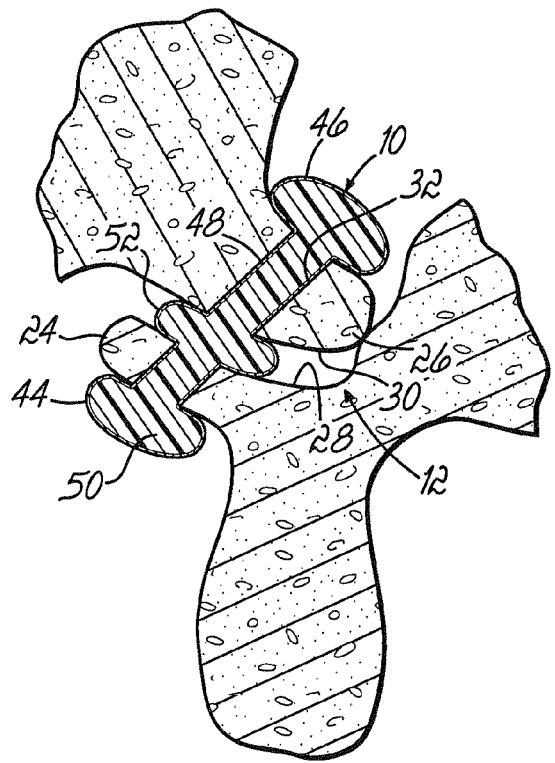
FIG. 4 depicts a cross-sectional view of an alternate embodiment of an implant device and method for stabilizing the facet joint, wherein an intermediate portion of the elongated member distracts the superior and inferior articular facets.

FIG. 4 shows an alternate embodiment of the method of stabilizing the facet joint 12 wherein a central portion 52 of the intermediate portion 48 of the elongated bag 10 expands beyond the hole 32 within the facet joint 12 such as to distract the opposing superior and inferior articular processes 24, 26.

While the elongated bag 10 has been discussed above, and illustrated, as being inserted first through the inferior articular process 26, it should be understood by one having ordinary skill in the art that the elongated bag 10 may be inserted first through the superior articular process to provide the elongated bag 10 in a reverse orientation. In other words, the elongated bag 10 may alternatively be positioned lengthwise in the hole 32 such that the first end portion 44, or closed end, is positioned proximate the inferior articular process opening 38 and the second end portion 46 is positioned proximate the superior articular process opening 40 of the hole 32.

The method of the present invention is understood to have a number of advantageous over other techniques. For example, the present method is minimally invasive as compared to other treatments that use facet screws, for example, which require dissection of muscle tissue and ligaments. In addition, other implant devices require additional mechanical manipulation following insertion, necessitating further disturbance and retraction of tissue. Also, unlike other implant devices, the filled, elongated bag 10 is not susceptible to displacement or migration from the facet joint 12 over time even though no additional straps or wires, for example, are used to hold the bag 10 in place.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative method and illustrative examples shown and described. Accordingly, departures may be made from such details without departing from the scope of the general inventive concept.

What is claimed is:
1. A method for stabilizing a facet joint comprising:
forming a hole through a facet joint and respective overlapping superior and inferior articular processes of adjacent vertebra which, respectively, include superior articular process and inferior articular process openings, the hole extending lengthwise between the superior articular process and inferior articular process openings;
inserting an elongated member lengthwise into the hole to position opposing first and second end portions of the member proximate either the superior articular process and inferior articular process openings, respectively, or the inferior and superior articular process openings, respectively, wherein the first end portion defines a closed end and the second end portion defines an open end permitting entry into an interior of the member; and
filling the interior of the member with a desired material to expand the first and second end portions of the member beyond respective superior articular process and inferior articular process openings of the hole to greater than a desired size of the superior articular process and inferior articular process openings to stabilize the facet joint.

2. The method of claim 1 wherein the step of forming the hole through the facet joint and respective overlapping superior and inferior articular processes of adjacent vertebra comprises drilling the hole posteriorly through the facet joint.

3. The method of claim 1 wherein the step of inserting an elongated member comprises inserting the elongated member lengthwise into the hole to position opposing first and second end portions of the member proximate the superior articular process and inferior articular process openings, respectively, and wherein filling the member comprises filling the member with the desired material to expand the first and second end portions of the member, respectively, beyond superior articular process and inferior articular process openings.

4. The method of claim 1 further comprising, after filling the interior of member, sealing the open end of the member.

5. The method of claim 1 wherein the step of inserting an elongated member lengthwise into the hole comprises via a delivery catheter, inserting the elongated lengthwise into the hole and wherein filling the member with a desired material comprises via the delivery catheter, filling the member with the desired material.

6. The method of claim 1 wherein the desired material is a flexible material.

7. The method of claim 1 wherein the elongated member is a bag that contains the desired material.

8. A method for stabilizing a facet joint comprising:
   forming a hole through a facet joint and respective overlapping superior and inferior articular processes of adjacent vertebra which, respectively, include superior articular process and inferior articular process openings, the hole extending lengthwise between opposing inferior and superior openings of a desired size;
   inserting an elongated member lengthwise into the hole, the member including opposing first and second end portions, the first and second end portions are positioned proximate either the superior articular process and inferior articular process openings, respectively, or the inferior and superior articular process openings, respectively, wherein the first end portion defines a closed end and the second end portion defines an open end permitting entry into an interior of the member and a central portion of the member between opposing first and second end portions is configured to expand; and
   filling the interior of the member with a desired material to expand the central portion beyond the hole within the facet joint thereby distracting the inferior and superior articular processes and to expand the opposing first and second end portions beyond respective superior articular process and inferior articular process openings of the hole to greater than a desired size of the superior articular process and inferior articular process openings to stabilize the facet joint.

9. The method of claim 8 wherein the step of forming the hole through the facet joint and respective overlapping superior and inferior articular processes of adjacent vertebra comprises drilling the hole posteriorly through the facet joint.

10. The method of claim 8 wherein the step of inserting an elongated member comprises inserting the elongated member lengthwise into the hole to position opposing first and second end portions of the member proximate the superior articular process and inferior articular process openings, respectively, and wherein filling the member comprises filling the member with the desired material to expand the central portion beyond the hole within the facet joint and to expand the first and second end portions of the member, respectively, beyond superior articular process and inferior articular process openings.

11. The method of claim 8 further comprising, after filling the interior of member, sealing the open end of the member.

12. The method of claim 8 wherein the step of inserting an elongated member lengthwise into the hole comprises via a delivery catheter, inserting the elongated lengthwise into the hole and wherein filling the interior of the member with a desired material comprises via the delivery catheter, filling the interior of the member with the desired material.

* * * * *